US00PP17146P2

(12) United States Plant Patent
Stahlhut

(10) Patent No.: US PP17,146 P2
(45) Date of Patent: Oct. 10, 2006

(54) CARNATION PLANT NAMED 'CFPC UNFORGETTABLE'

(50) Latin Name: *Dianthus caryophyllus*
Varietal Denomination: CRPC Unforgettable

(75) Inventor: Roy Stahlhut, Watsonville, CA (US)

(73) Assignee: California Florida Plant Company, Salinas, CA (US)

( * ) Notice: Subject to any disclaimer, the term of this patent is extended or adjusted under 35 U.S.C. 154(b) by 0 days.

(21) Appl. No.: 11/177,864

(22) Filed: Jul. 8, 2005

(51) Int. Cl.
*A01H 5/00* (2006.01)

(52) U.S. Cl. ..... Plt./272
(58) Field of Classification Search ..... Plt./272
See application file for complete search history.

(56) References Cited

U.S. PATENT DOCUMENTS

PP14,843 P2 6/2004 Hasegawa ..... Plt./273

OTHER PUBLICATIONS

2001–2002 California Florida Plant Company brochure showing the variety 'CFPC Sari' at p. 4.

*Primary Examiner*—Kent Bell
*Assistant Examiner*—Annette H Para
(74) *Attorney, Agent, or Firm*—Winston & Strawn, LLP

(57) ABSTRACT

A new variety of carnation plant named 'CFPC Unforgettable' having flowers with a light to medium purple color diffused over a cream base color. The center of the flowers are cream color with a faint purple pigmentation gradually becoming darker purple toward the petal edge. The flower coloring gives the new variety a distinctive "watercolor" effect.

1 Drawing Sheet

Latin name of the genus and species: Botanical classification: *Dianthus caryophyllus.*

Variety denomination: The new carnation variety denomination is 'CFPC Unforgettable'.

BACKGROUND OF THE INVENTION

The present invention comprises a new and distinct cultivar of hybrid carnation botanically known as *Dianthus caryophyllus*, and referred to by the cultivar name 'CFPC Unforgettable'.

'CFPC Unforgettable', identified as selection no. 020135, originated from a cross made by Roy Stahlhut in a controlled breeding program in Salinas, Calif.

The female parent of the new variety is the patented variety known as 'CFPC Sari' (U.S. Plant Pat. No. 14,843) and the male parent is the unpatented variety known as selection no. 000809-6. The new variety 'CFPC Unforgettable' has been asexually reproduced by vegetative side shoot cuttings in Salinas, Calif. and the distinguishing characteristics are retained through successive generations of asexual reproduction.

BRIEF SUMMARY OF THE INVENTION

'CFPC Unforgettable' is a potted spray-type of carnation plant variety having flowers with a light to medium purple color diffused over a cream base color. The center of the flowers are cream color with a faint purple pigmentation gradually becoming darker purple toward the petal edge. The flower coloring gives the new variety a distinctive "watercolor" effect.

COMPARISON WITH FEMALE PARENT

Plants of the new carnation variety 'CFPC Unforgettable' are similar to the female parent 'CFPC Sari' in plant habit and growth rate. In side-by-side comparisons in Salinas, Calif., under commercial practice, plants of the new carnation variety 'CFPC Unforgettable' differed from plants of the female parent 'CFPC Invitation' in at least the following characteristic:

1. The new variety 'CFPC Unforgettable' produces flowers with light to medium purple color diffused over a cream base color whereas the female parent 'CFPC Sari' produces flowers having a yellow base color and purple picotee.

COMPARISON WITH MALE PARENT

Plants of the new carnation variety 'CFPC Unforgettable' are dissimilar to the male parent selection no. 000809-6 in plant habit and growth rate, and differed from plants of the male parent in the following characteristics:

1. The new variety 'CFPC Unforgettable' produces flowers with light to medium purple color diffused over a cream base color while the male parent selection no. 000809-6 produces purple flowers.
2. The new variety 'CFPC Unforgettable' has a smaller growth habit when compared to the larger spreading habit of the male parent.
3. The new variety 'CFPC Unforgettable' produces flowers that are less laciniated than the male parent.

BRIEF DESCRIPTION OF ILLUSTRATION

Typical specimens of the plant and flowers for the new carnation variety 'CFPC Unforgettable' are shown in the accompanying photograph. The colors shown are as true as possible within the usual limits of this kind of illustration.

FIG. 1 is a whole plant view of the new variety 'CFPC Unforgettable' grown in a pot. The plant shown in the illustration is 120 days from date of planting.

DETAILED BOTANICAL DESCRIPTION

The following description of the new carnation variety 'CFPC Unforgettable' is of plants 120 days from the date of planting grown in a commercial greenhouse in Salinas, Calif. in the month of December. The cultivar has not been observed under all possible environmental conditions. The phenotype may vary significantly with variations in the environment such as temperature, length of day and light intensity without any variance in genotype.

Plants of the new variety have been grown successfully under temperature conditions averaging about 18° C. at night and about 24° C. to 28° C. during the day under light conditions of about 12 hours. Plants are daylight neutral and flower throughout the year. Chemical growth regulators are not required for production.

The new variety may be produced as a potted spray-type carnation. To produce a commercial product the plants may be pinched once with the center bud removed. Pinched plants are about 20.9 cm tall and about 20.9 cm in diameter. Flower diameter averages about 4.4 cm with a crown of about 1.0 cm. Foliage is generally about 13.2 cm long and about 0.8 cm at the widest point. The typical container size for commercial growth is 4½ inches. It has been observed that the shelf life of the new variety is about 21 days with the first appearance of color in the buds occurring at about 80–90 days after planting of cuttings. The commercial classification of the new carnation variety is a potted spray-type.

The following description is with respect to a plant produced as a potted spray-type. The plant and flower measurements and foliage size are established as an average using standard commercial cultural practices. In the description of this new carnation variety, color values have been taken from The Royal Horticultural Society Colour Chart (R.H.S.C.C.).

PLANT

Height (cm): 20.9.
Form: Herbaceous.
Growing habit: Semi-upright.
Branching characteristics: 5–6 laterals per stem.
Breaking action: 5–6 breaks per plant with strong straight stems.
First appearance of color in buds: Very early flowering, 80–90 days after planting.
Vigor: Excellent.
Shelf life: 21 days.
Blooming habit: Spray type.
Blooming season: Year round.
Lastingness of blooms: About 10 days.
Disease (susceptibility/resistance observed): Good resistance to soil-borne diseases such as *Fusarium oxysporum* and *F. graminearium*, and root rots such as damping off, water molds and similar types, as is typical of carnations.
Pest (susceptibility/resistance observed): None observed.
Drought and temperature (susceptibility/resistance observed): None observed.
Mutation prone: No.
Propagation:
*Type.*—Side shoot cuttings.
*Time to rooting.*—18 days with soil temperatures of 18° C. to 21° C.
*Rooting habit.*—Good fibrous system.
Growth treatments or special conditions: None.

FOLIAGE

Stem:
*Diameter.*—Base (cm): 0.5.
*Texture.*—Smooth.
*Cross section.*—Edged.
*Color.*—Internode: 137A. Node: 139D.
Number of leaves per lateral branch: 18–20.
Arrangement of leaves: Bi-lateral along the stem.
*Shape of leaf.*—Long, narrow, lanceolate.
*Size of leaf.*—Width (cm): 0.8. Length (cm): 13.2.
*Leaf apex.*—Acute.
*Edge.*—Smooth.
*Surface texture.*—Top: smooth. Bottom: smooth.
Leaf venation: Prominent mid-vein at underside.
Leaf longitudinal axis: Recurved.
Leaf cross section (upper side): Weakly concave.
Leaf color: Mature leaf, upper side: 147A. Under side: 137B.
Leaf waxy layer: Weak.

FLOWER

Flower appearance: Matte.
Flower type: Semi-double.
Flower profile of upper part of corolla: Flat convex.
Flower profile of lower part of corolla: Concave.
Flower shape: Flattened dome, round.
Number of blossoms per branch: 18–20.
Depth of fully expanded blossoms (cm): 1.0.
Diameter of fully expanded blossoms (cm): 4.4.
Calyx:
*Sepals number.*—5.
*Length (cm).*—0.5.
*Width (cm).*—0.4.
*Color.*—Outer side: Middle to tip: 144B. Base: 144C. Inner side: 138C.
*Texture.*—Smooth.
*Appearance.*—Matte.
*Shape.*—Cylindrical.
Flower petals:
*Form/shape.*—Fan shaped.
*Petal edge.*—Edge type: Serrate. Laciniated: Width (mm): 1–2. Depth (mm): 4–5.
*Texture.*—Smooth.
*Appearance.*—Matte.
*Petal surface of blade.*—Undulating.
*Number per flower.*—23.
*Outer petals.*—Length (cm): 4.2. Width (cm): 1.7.
*Inner petals.*—Length (cm): 4.2. Width (cm): 1.7.
Fragrance: None to slight.
Flower bud (at onset of color):
*Length (cm).*—2.4.
*Diameter (cm).*—0.8.
*Form/shape.*—Ovoid.
Flower color:
1. *General tonality.*—Cream with diffused light purple.
2. *Petals, upper surface.*—Gradient of 155D at center of petal to 75A at petal edge with occasional pencil marks of 75A along the length of the petal.
3. *Petals, lower surface.*—Lighter than 155D at center with gradient to 75A at petal edge.
4. *Petals, edge.*—75A.

5. *Petals, center.*—Lighter than 155D with gradient to 75A.
6. *Early bud.*—75A.

Color distribution: Edged-striated-speckled.
Petal macule: Absent.
Flower progression with age: Retains color very well.

REPRODUCTIVE ORGANS

Gynoecium: Pistillate.
*Pistil number.*—1.
*Pistil length* (*cm*).—2.7.
*Pistil color.*—Whiter than 155D.
*Stigma number.*—2 and 3.
*Stigma color.*—Whiter than 155D with faint 75C tips.
*Stigma shape.*—Filamentous.
*Style color.*—Whiter than 155D.
*Style number.*—2 and 3.

Ovary:
*Shape.*—Ellipsoid.
*Surface.*—Smooth.
*Color.*—Base: 145D. Body: 144C. Apex: 144C.

Androecium: None produced.
Fruit and seeds: None produced.

What is claim is:

1. A new and distinct variety of carnation plant, substantially as described and illustrated herein.

* * * * *

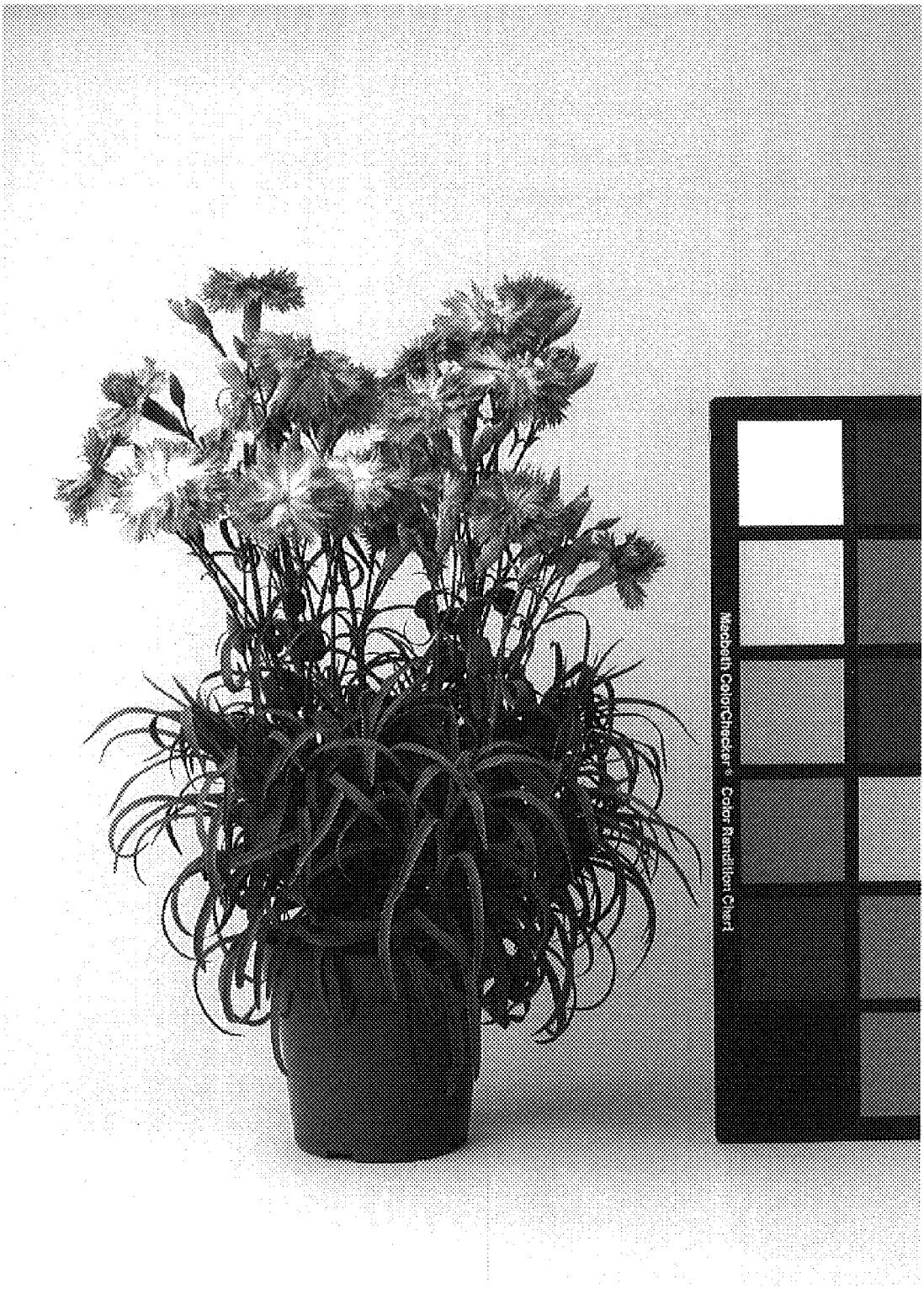
MacBeth ColorChecker® Color Rendition Chart